(12) United States Patent
Hasegawa

(10) Patent No.: US 10,383,540 B2
(45) Date of Patent: Aug. 20, 2019

(54) COGNITIVE FUNCTION EVALUATION APPARATUS, METHOD, SYSTEM AND PROGRAM

(71) Applicant: National Institute of Advanced Industrial Science and Technology, Tokyo (JP)

(72) Inventor: Ryohei Hasegawa, Ibaraki (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 282 days.

(21) Appl. No.: 15/113,258

(22) PCT Filed: Dec. 16, 2014

(86) PCT No.: PCT/JP2014/083248
§ 371 (c)(1),
(2) Date: Jul. 21, 2016

(87) PCT Pub. No.: WO2015/111331
PCT Pub. Date: Jul. 30, 2015

(65) Prior Publication Data
US 2017/0007147 A1    Jan. 12, 2017

(30) Foreign Application Priority Data
Jan. 23, 2014 (JP) ................. 2014-010509

(51) Int. Cl.
*A61B 5/0484* (2006.01)
*A61B 5/16* (2006.01)
(Continued)

(52) U.S. Cl.
CPC ...... *A61B 5/04842* (2013.01); *A61B 5/04012* (2013.01); *A61B 5/0478* (2013.01);
(Continued)

(58) Field of Classification Search
None
See application file for complete search history.

(56) References Cited

U.S. PATENT DOCUMENTS

2003/0013981 A1* 1/2003 Gevins ................ A61B 5/0484
600/544
2013/0158883 A1* 6/2013 Hasegawa ............ A61B 5/0476
702/19

FOREIGN PATENT DOCUMENTS

JP    2003522580 A    7/2003
JP    2004535231 A    11/2004
(Continued)

OTHER PUBLICATIONS

Hasegawa, Ryohei, et al. "Single trial-based prediction of a go/no-go decision in monkey superior colliculus," Neural Networks 19 (2006), pp. 1223-1232.
(Continued)

*Primary Examiner* — Etsub D Berhanu
(74) *Attorney, Agent, or Firm* — Cantor Colburn LLP (57) ABSTRACT

Provided are a cognitive function evaluation apparatus, a cognitive function evaluation method and system, and a program that can be implemented for non-handicapped persons and persons with severe motor impairment. The apparatus according to the present invention is an apparatus for evaluating cognitive function provided with a processing unit that analyzes and processes a brain wave caused by a plurality of stimulus events including a target and a non-target; estimates a stimulus event selected as the target from the plurality of stimulus events; determines a discrimination score or decoding accuracy; and evaluates cognitive function on the basis of a value of one or more of the discrimination score, the decoding accuracy, any of time courses, and decoding speed. With respect to two or more stimulus event groups having different levels of difficulty distinguish-
(Continued)

ing between stimulus events, a discrimination score or decoding accuracy may be determined for each of the different difficulty levels, and cognitive function may be evaluated on the basis of a connection between one or more of the discrimination score, the decoding accuracy, any of time courses, and decoding speed and the difficulty levels.

18 Claims, 5 Drawing Sheets

(51) Int. Cl.
*A61B 5/00* (2006.01)
*A61B 5/04* (2006.01)
*A61B 5/0478* (2006.01)
*A61F 4/00* (2006.01)

(52) U.S. Cl.
CPC .......... *A61B 5/04845* (2013.01); *A61B 5/162* (2013.01); *A61B 5/168* (2013.01); *A61B 5/6803* (2013.01); *A61B 5/7264* (2013.01); *A61F 4/00* (2013.01)

(56) References Cited

FOREIGN PATENT DOCUMENTS

| | | | |
|---|---|---|---|
| JP | 2009542276 | A | 12/2009 |
| JP | 2010274035 | A | 12/2010 |
| JP | 2012053656 | A | 3/2012 |
| JP | 2012073329 | A | 4/2012 |
| JP | 2013042768 | A | 3/2013 |
| JP | 2013178601 | A | 9/2013 |
| WO | WO-2012029742 | A1 * | 3/2012 ........... A61B 5/0476 |

OTHER PUBLICATIONS

International Search Report, PCT/JP2014/083248, dated Mar. 31, 2015, pp. 1-2.
Matsumoto, N. et al. "Prediction of Multi-Dimensional Decision-Making Based on Single-Trial Activities of A Population of Prefrontal Neurons," Neuroscience Research, vol. 58, Supplement 1, (2007), pp. S1-S244.
McClure, Samuel M., et al. "Neural Correlates of Behavioral Preference for Culturally Familiar Drinks," Neuron, vol. 44, pp. 379-387, Oct. 14, 2004.

* cited by examiner

First game

Target: ID-1
Maximum discrimination score: ID-1
(successful decoding)

COGNITIVE FUNCTION EVALUATION APPARATUS, METHOD, SYSTEM AND PROGRAM

TECHNICAL FIELD

The present invention relates to apparatus, methods, systems, and programs for objectively evaluating the cognitive function of a test subject by measuring and analyzing brain activity of the test subject.

BACKGROUND ART

The progress that has been made in recent years in brain science has led to various studies on the relationship between human thought or behavior and brain activity. Attention is being focused on Brain-Machine Interface (BMI) technology for controlling external equipment or conveying one's intention to another person by noting a biosignal of, e.g., brain activity.

For example, neuromarketing is the study for investigating the brain activity related to consumer behavior using a functional MRI (fMRI) device or the like. A study is known in which, based on a brain activity measurement experiment using a fMRI apparatus, brain areas related to preferences or brand awareness were identified and brain activity differences were investigated (see Non Patent Literature 1).

The present inventor has shown, using a measurement technique involving extracellular recording of the action potential of a single neuron via electrodes placed in an animal brain, and by a simulation of neuronal ensemble activity, that the representation of relationships among a plurality of external stimuli (experimental conditions) in the brain can be estimated in terms of low-dimensional spatial information (see Non Patent Literature 2). However, many aspects of brain activity are still unknown, and the measurement methods have limitations.

The present inventor has also proposed a virtual decision function, and shown a calculation method therefor (see Non Patent Literature 3). Non Patent Literature 3 describes a method for predicting an alternative behavior from a neural activity such as a single neural activity.

The present inventor has also proposed an intention conveyance assist apparatus and method for conveying an intention by brain activity analysis (see Patent Literatures 1 and 2). The technology according to Patent Literatures 1 and 2 assists, for example, the conveyance of an intention of a person with motor impairment having difficulty speaking or writing, or of a person with severe motor impairment having difficulty performing an input operation on various devices using hands or legs. Particularly, in the field of nursing care/welfare device development, people such as the elderly or the sick may be unable to perform a complex input operation, require training to learn an operation method, or even have difficulty learning. The technology according to Patent Literatures 1 and 2 has enabled direct transmission of an intention without requiring a special operation. Further, the apparatus according to Patent Literatures 1 and 2 has enabled patients with speech impediment or the elderly to convey their intentions regarding basic personal care or feelings to the helper in simpler manner.

The present inventor has proposed a technique for showing a map of information representations in the brain by brain wave analysis performed on general test subjects, including non-handicapped persons (see Patent Literature 3). The present inventor has also proposed an apparatus and method for ranking by brain wave analysis the objects to be investigated (see Patent Literature 4). According to the technology of Patent Literature 4, the ranking of the objects to be investigated enables ranking of information about brain activity including both conscious awareness and subconscious awareness, which can be effectively utilized for marketing study and the like.

A prior-art search has identified a proposal to characterize a neural functional state of a test subject by the steps of feeding a stimulus to the test subject and monitoring a brain wave reaction during a neural activity caused by the stimulus, and to compare the brain wave reaction with the results obtained from other test subjects or a group of test subjects, or with the results obtained from the same test subject under different conditions (see Patent Literature 5). Another technology has also been proposed whereby an environment change determination unit is provided to determine whether a test subject has been given a stimulus by a change deviating from steady state in the environment around the test subject, and, if it is determined that the stimulus has been given, an event-related potential corresponding to the stimulus is detected to calculate, based on a feature quantity obtained from the potential, a value indicating the degree of concentration of the test subject (see Patent Literature 6).

CITATION LIST

Patent Literature

Patent Literature 1: JP 2012-053656 A
Patent Literature 2: JP 2012-073329 A
Patent Literature 3: JP 2010-274035 A
Patent Literature 4: JP 2013-178601 A
Patent Literature 5: JP 2003-522580 T
Patent Literature 6: JP 2013-042768 A

Non Patent Literature

Non Patent Literature 1: McClure S M, et al., "Neural Correlates of Behavioral Preference for Culturally Familiar Drinks" Neuron 44, p 379-387, 2004.
Non Patent Literature 2: N. Matsumoto and R. Hasegawa, "Prediction of Multidimensional Decision-making Based on Single Trial of Frontal Association Area Neuronal Ensemble", Neuroscience Research, vol. 58, Supplement 1, page S161 (P2-f34), 2007.
Non Patent Literature 3: R. Hasagawa, et al., "Single trial-based prediction of a go/no-go decision in monkey superior colliculus", Neural Networks 19 (2006) 1223-1232.

SUMMARY OF INVENTION

Technical Problem

The problem to be solved by the conventional technology according to Patent Literatures 1 and 2 was to decode an intention decision in the brain at high speed and with high accuracy by analyzing brain wave data.

The proposal made by the present inventor in Patent Literature 1 will be described in detail.

The technology according to Patent Literature 1 solves the problem that the devices proposed earlier by the studies on intention transmission have too much noise for the measurement of biological information, such as brain waves, resulting in a low probability of correct results and a long time before a determination can be made. Particularly, the technology according to Patent Literature 1 makes it possible to discriminate an intention in the brain without erroneous determinations and in a short time, enables a device to be operated directly and in real-time by a thought in the operator's brain, and permits a patient with speech impediment or the elderly to convey intentions regarding basic personal care or feelings to the helper directly and more simply.

The technology according to Patent Literature 1 was achieved by a technique for quantifying the process of intention decision in the brain using a "virtual decision function" previously studied and developed by the present inventor. In Patent Literature 1, the concept of virtual decision function is greatly expanded and utilized as a technique for decoding intentions in the brain for an intention conveying apparatus based on brain wave measurement. The literature also proposes a technique whereby the brain wave decoding is terminated and an answer is given when a sufficiently high prediction probability is achieved.

The intention conveyance assist apparatus according to Patent Literature 1 includes a stimulus presentation apparatus and a processing apparatus for processing brain wave data from an electroencephalograph that measures a brain wave after stimulus presentation by the stimulus presentation apparatus, and is characterized in that the processing apparatus determines that a specific intention decision has been made in the brain on the basis of a discriminant function obtained by analyzing the brain wave data and a success rate. When the product of an accumulated discrimination score according to the discriminant function obtained by analyzing the brain wave data and the success rate exceeds a threshold value, it is determined that the specific intention decision has been made in the brain, and a determination result is output to a device. Patent Literature 1 describes that the function obtained by analyzing the data measured by the electroencephalograph is a multivariate analysis function, such as a logistics function or a linear discriminant analysis function, where weighting of variables are set for each brain wave channel and at intervals of elapsed time after stimulus presentation. It also describes that an alternative intention decision may preferably be utilized. In addition, the literature describes that by appropriately adjusting the threshold value by prior simulation, a setting as to whether prediction accuracy or prediction speed is to be given priority, and a setting such that they are balanced may be selected.

The technology according to Patent Literature 1 enables an intention in the brain to be decoded in real-time to assist the conveyance of the intention, where the success rate is used as a numerical value for generating an improved virtual decision function.

The present inventor, during the course of studies on the decoding of brain activity information, realized that among the persons with serious motor impairment, patients, or the elderly and the like who have difficulty speaking or writing or difficulty making an input operation on a device using hands or legs, some have impairments not only in motor function but also cognitive function, in which case they cannot properly use the device.

For example, when an intention decision is decoded by an apparatus such as according to Patent Literature 1 using a brain wave, use of the apparatus requires that a certain degree of cognitive function remain intact. Accordingly, the presence or absence of cognitive function impairment or its degree needs to be determined.

A non-handicapped person, when subjected to a stimulus in any of the various senses (for example, vision, hearing, taste, and touch) via the eye, ear and the like, a cognitive function corresponding to the stimulus is activated, and the motor function for moving hands or legs, speaking, or writing is activated in accordance with the cognitive function. Conventionally, it has been known that the presence or absence of cognitive function impairment can be determined by a testing technique involving the execution of a cognitive task, for example. However, when there is serious motor function impairment making speech or writing difficult, it is often difficult to employ the existing cognitive function evaluation method.

The present invention aims to overcome the above problems and an object of the present invention is to evaluate cognitive function. An object of the present invention is to evaluate, in a preparation stage for using an intention conveyance assist apparatus based on a brain wave, the cognitive function of an operator. An object of the present invention is to examine and evaluate, regardless of whether the intention conveyance assist apparatus based on a brain wave is to be used or not, the cognitive function of the test subject. Another object of the present invention is to achieve cognitive function evaluation based on physiological data for not only persons with motor impairment but also persons without motor problems. Another object of the present invention is to enable early discovery of cognitive function impairment and to train and enhance cognitive function by evaluating the cognitive function based on a brain wave.

Solution to Problem

In order to achieve the objects, the present invention has the following features.

A cognitive function evaluation apparatus according to the present invention includes a processing unit that analyzes and processes a brain wave caused by a plurality of stimulus events including a target and a non-target, estimates a stimulus event selected as the target from the plurality of stimulus events, determines a discrimination score or decoding accuracy, and evaluates cognitive function on the basis of a value of one or more of the discrimination score, the decoding accuracy, any of time courses, and decoding speed. A cognitive function evaluation apparatus according to the present invention includes a processing unit that, with respect to two or more stimulus event groups having different levels of difficulty distinguishing between the stimulus events, analyzes and processes a brain wave caused by a plurality of stimulus events including a target and a non-target, estimates a stimulus event selected as the target from the plurality of stimulus events, determines a discrimination score or decoding accuracy for each of the different difficulty levels, and evaluates cognitive function on the basis of a connection between one or more of the discrimination score, the decoding accuracy, any of time courses, and decoding speed and the difficulty levels.

A cognitive function evaluation method according to the present invention includes analyzing a brain wave caused by a plurality of stimulus events including a target and a non-target; estimating a stimulus event selected as the target from the plurality of stimulus events; determining a discrimination score or decoding accuracy; and evaluating cognitive function on the basis of a value of one or more of the discrimination score, the decoding accuracy, any of time courses, and decoding speed. A cognitive function evaluation method according to the present invention includes, with respect to two or more stimulus event groups having different levels of difficulty distinguishing between stimulus events, analyzing a brain wave caused by a plurality of stimulus events including a target and a non-target; estimating a stimulus event selected as the target from the plurality of stimulus events; determining a discrimination score or decoding accuracy for each of the different difficulty levels; and evaluating cognitive function on the basis of a connection between one or more of the discrimination score, the decoding accuracy, any of time courses, and decoding speed and the difficulty levels. The levels of difficulty distinguishing between the stimulus events may be modified by subjecting a stimulus event image to image processing.

A cognitive function evaluation system according to the present invention includes a stimulus presentation apparatus for presenting a stimulus; an electroencephalograph; and a processing apparatus for processing brain wave data from the electroencephalograph. The stimulus presentation apparatus presents a plurality of stimulus events including a target and a non-target each a plurality of times. The electroencephalograph measures a brain wave immediately after stimulus presentation by the stimulus presentation apparatus. The processing apparatus analyzes and processes a brain wave caused by the plurality of stimulus events including a target and a non-target, estimates a stimulus event selected as the target from the plurality of stimulus events, determines a discrimination score or decoding accuracy, and evaluates cognitive function on the basis of a value of one or more of the discrimination score, the decoding accuracy, any of time courses, and decoding speed.

A program according to the present invention causes a computer to function as: a stimulus presentation means for presenting a plurality of stimulus events each a plurality of times; a processing means for analyzing and processing brain wave data of an event-related potential immediately after the stimulus presentation, estimating a stimulus event selected as the target from the plurality of stimulus events, determining a discrimination score or decoding accuracy, and evaluating cognitive function on the basis of a value of one or more of the discrimination score, the decoding accuracy, any of time courses, and decoding speed; and a presenting means for presenting a cognitive function evaluation result.

Advantageous Effects of Invention

According to the present invention, a brain wave is analyzed and expressed in numerical value so as to enable cognitive function to be evaluated according to an objective index. Because the cognitive function can be represented by a single value (of decoding accuracy in a range of 0 to 100%, for example) for a single experiment on a single test subject, absolute evaluation can be made as long as experiment conditions are fixed. In addition, relative evaluation of an individual versus a group (non-handicapped person range) can also be performed.

According to the present invention, in a preparation stage for using an intention conveyance assist apparatus based on a brain wave, the operator's cognitive function can be evaluated. Accordingly, intention conveyance assist can be more accurately executed. In addition, according to the present invention, the cognitive function of the test subject can be examined and evaluated regardless of whether the intention conveyance assist apparatus based on a brain wave is used.

According to the present invention, cognitive function evaluation can be achieved based on physiological data not only for persons with motor impairment, but also for people having no motor problem. Further, according to the present invention, cognitive function evaluation is performed using brain waves, enabling early discovery of cognitive function impairment. The present invention may also be utilized for training or enhancement of cognitive function of the test subject.

DESCRIPTION OF EMBODIMENTS

Embodiments of the present invention will be described in the following.

The present invention is aimed at evaluating cognitive function by analyzing a brain wave, where a cognitive task that can be analyzed based on the brain wave is provided so as to analyze brain activity. The cognitive task that can be analyzed based on the brain wave may have different difficulty levels, and the brain activity may be analyzed using such cognitive task.

According to the present invention, focusing on an event-related potential indicating the type of brain activity, particularly the brain wave recorded in the scalp, the cognitive function of the test subject is evaluated by analyzing the reaction of the brain to the presentation of a stimulus event. Specifically, the present invention mainly includes the elements of stimulus event presentation, brain wave measurement, brain wave data analysis, and presentation of a cognitive function evaluation result.

First Embodiment

Figure 1:
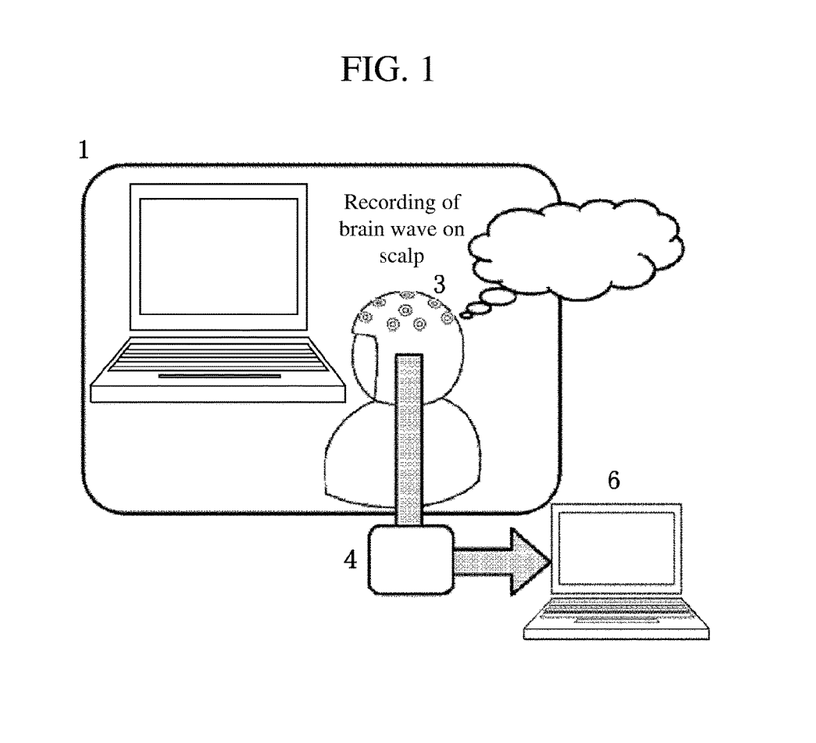
FIG. 1 is a schematic diagram of an apparatus according to the present invention.

The present embodiment will be described with reference to the drawings. FIG. 1 is a diagram schematically illustrating an apparatus and method according to the present embodiment. FIG. 1 illustrates stimulus presentation 1 to a test subject, where the test subject is shown a display screen for stimulus presentation, and a brain wave in the scalp of the test subject is measured and recorded by an electroencephalograph (a brain wave amplifier 4 in the figure). The test subject for the implementation may include a general apparatus user, a non-handicapped person, a person with disability and requiring care, or the elderly. The test subject has electroencephalograph electrodes 3 attached to the head to measure a brain wave. For example, a head cap with the electroencephalograph electrodes affixed thereto is used. On a display screen (monitor), various visual stimuli are presented, and brain wave raw waveform data are obtained by the electroencephalograph. The brain wave raw waveform data are analyzed and processed by a processing apparatus such as a computer 6, and a cognitive function evaluation result is displayed on the display screen or the like. In FIG. 1, a bold arrow extending from the head portion where the brain wave electrodes are positioned to the brain wave amplifier 4, and further from the brain wave amplifier 4 to the computer 6, schematically indicates the conveyance of a signal in a wired or wireless manner.

Figure 2:
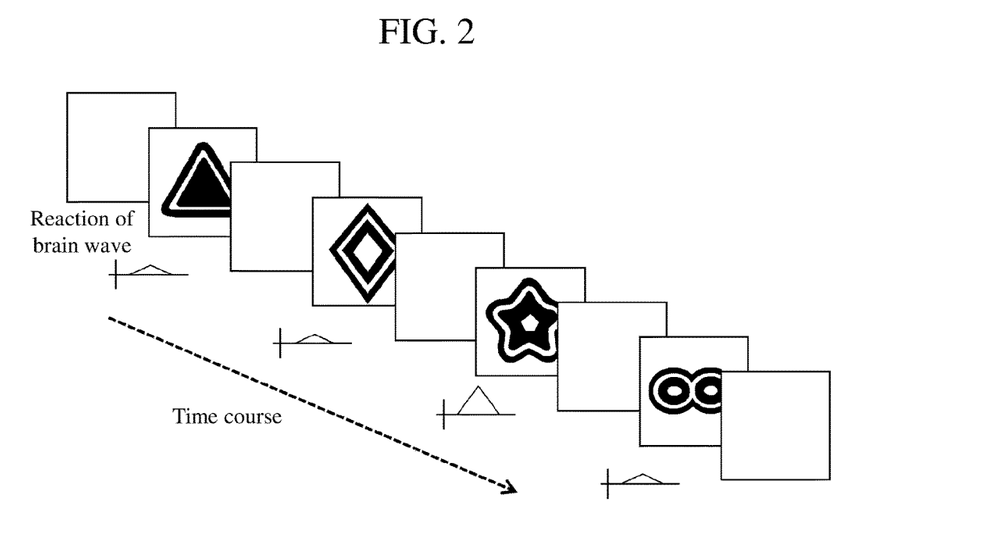
FIG. 2 is a schematic diagram illustrating a first embodiment.

FIG. 2 is a diagram schematically illustrating stimulus event presentations and brain wave reactions in the test subject according to the present embodiment, together with the time course. As illustrated in FIG. 2, stimulus events (also referred to as attention invoking events or test stimulus events), such as simple figures, are presented to the test subject one event (one sheet) at a time. Then, the brain wave of the test subject having seen the events is measured by the electroencephalograph with the electrodes attached to the head portion of the test subject, and the brain wave is analyzed by a brain wave analysis/processing apparatus, such as a computer. The stimulus events may include signs, illustrations, drawings, and photographs. At the bottom of FIG. 2, brain waves corresponding to a plurality of stimulus events are schematically shown for illustrating the present embodiment. Specifically, (a) stimulus event presentation and measurement of brain waves in response to the stimulus events, and (b) a brain wave data analysis process and a cognitive function evaluation process are implemented as follows.

(a) Stimulus Event Presentation and Measurement of Brain Waves in Response to Stimulus Events The test subject is taught one of a plurality of stimulus events, such as eight figures, as a target. Then, a cognitive task involving counting the number of times that the target was presented among the successively presented stimulus events in the head is implemented for the test subject while the brain wave is measured. The brain wave is measured from one or a plurality of electrodes installed on the scalp around the top of the head at the center. The measurement is performed by the following procedure. The electrodes are positioned at 8 locations according to a standard electrode locating method (10% method).

(1) A plurality of visual stimuli (for example, figures, illustrations, drawings, photographs, moving images and the like) is presented to the test subject. For example, visual stimuli (simple figures in FIG. 2) are successively presented in a pseudo-random sequence, as in a picture-story show, on the display screen of a computer (see FIG. 2). The visual stimuli are merely an example, and other stimuli, such as hearing stimuli (sounds, voices, music or the like), touch stimuli, or odor stimuli may be employed.

(2) Before the presentation, the test subject is taught that one (such as star) of the plurality of visual stimuli (which in FIG. 2 are a plurality of geometric figures including triangle, rhombus, star, double-ellipse, quadrangle, circle, heart, and clover) is the target. While each of the visual stimuli is presented a plurality of times, the test subject is taught to count the number of times of presentation of only the target stimulus in the head. This constitutes one game. For example, during one game, a block in which the visual stimuli are each presented once in a pseudo-random order (a unit of a round of stimulus presentation) is successively repeated five times. In this case, each and every visual stimulus is presented five times. The time per presentation of each visual stimulus is 750 milliseconds, and the next visual stimulus is presented after a blank of 250 milliseconds.

(3) After a short rest, another game, i.e., (2), is executed with the teaching of the target stimulus event successively varied. This is repeated until all of the plurality of visual stimuli have been presented as the target. For example, when the implementation involves eight figures, eight games are implemented in total. If the test subjects use a common target so that the experiment results can be compared, it may not be necessary to implement all of the games. Conversely, as long as a common target is used, the same game may be performed a plurality of times.

The above items (2) and (3) will be described in greater detail. For example, brain wave data are obtained when all of the types have been made the target, such as the first target being the star; the second target being the triangle; the third target being the rhombus; and the fourth target being the quadrangle, and when the types are not made the target. The brain wave data shown at the bottom of FIG. 2 are an example of the brain wave data corresponding to the respective visual stimuli when the test subject is taught the star as the target and asked to count the target from the visual stimuli shown. As illustrated schematically, the brain wave data corresponding to the visual stimulus of the target (star) show a greater reaction in terms of brain wave than the brain wave data corresponding to the visual stimuli of non-targets (triangle, rhombus, and double-ellipse). Similarly, when the test subject is taught other targets, the brain wave data corresponding to the target visual stimulus in most cases showed greater reactions in brain wave than the brain wave data corresponding to the non-target test stimuli.

The present inventor, on the assumption that the brain wave data corresponding to the target visual stimulus do not necessarily show a greater brain wave reaction than the brain wave data corresponding to non-target test stimuli because the brain wave data are related to the cognitive function level of the test subject, focused on decoding accuracy as a cognitive function index, and expressed the decoding accuracy in numerical value.

The brain wave as it relates to the test stimuli (such as visual stimuli, hearing stimuli, odor stimuli, or touch stimuli) will be described. According to the present embodiment, a brain wave potential referred to as "event-related potential" (or "event-related brain wave") in response to the test stimulus is utilized. The event-related potential is a transient brain wave produced in conjunction with the timing of occurrence of an external or internal event affecting the cognitive process. An example of the brain wave is referred to as "P300" (positive potential change 300 milliseconds after the presentation of stimulus).

Figure 8:
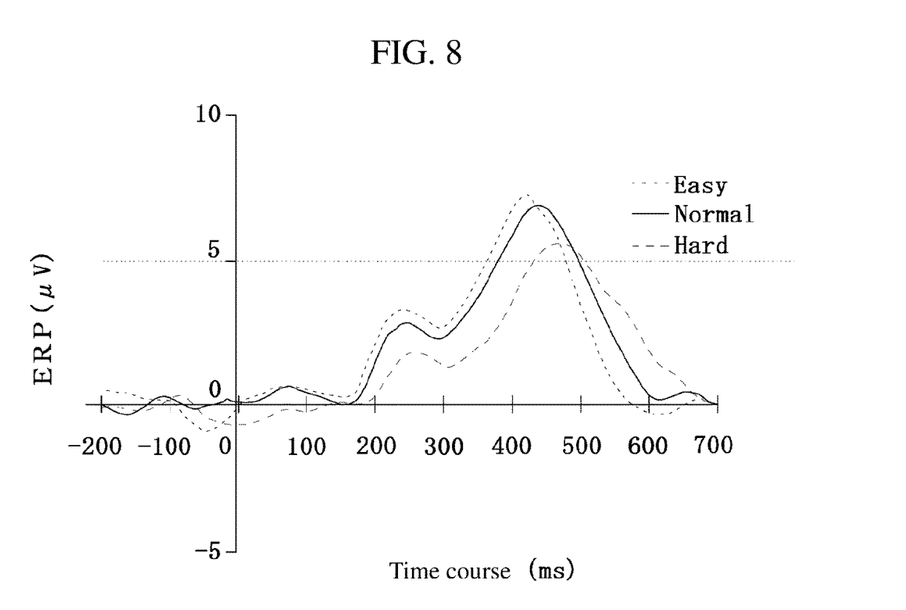
FIG. 8 is a diagram illustrating brain wave data in the stimulus event groups with different difficulty levels in the second embodiment.

FIG. 8 schematically illustrates an example of the event-related potential, of which the details will be described later. The three curves show examples of the brain waves observed in response to the target when the test stimulus objects (such as geometric figures) were closely watched and selected (i.e., when the target was consciously selected under active target-search conditions such that the selection or search is conducted while being aware of the target and non-target). While not shown in the drawing, the brain waves when the test stimulus objects were closely watched but not selected (because they were regarded as non-targets), the amplitude was smaller.

(b) Brain Wave Data Analysis Process and Cognitive Function Evaluation Process

According to the present embodiment, in order to represent the intensity of brain reaction by a single index, linear discriminant analysis is utilized. Other pattern recognition techniques may be used for quantitative representation.

Using a discriminant model expression generated based on a difference in brain wave data in response to the target or non-target set by the experimenter in each game, a discrimination score is calculated for each test stimulus event. The discrimination scores calculated for the test stimuli in each block are accumulated for each type of stimulus, and the test stimulus event that has earned the maximum accumulated discrimination score is estimated to be the test stimulus selected by the test subject in the brain. Depending on whether the estimated stimulus matches the actual target, the success or failure of decoding is determined for each game, and the ratio of the games among all of the games that resulted in successful decoding is considered the decoding accuracy.

The brain waveform patterns and the brain areas where a characteristic waveform appears vary greatly from one individual to another, and it is difficult to determine the cognitive function level only with the amplitude or latency of the event-related potential (mainly P300) as according to conventional technology. However, according to the present embodiment, decoding accuracy is expressed as a numerical value, thereby enabling objective and instantaneous estimation of the presence or absence and the degree of cognitive function impairment.

In the following, the embodiment will be described in detail with reference to mathematical expressions.

(b-1) Division of Data to Create Discriminant Model Expression

According to the present embodiment, data are divided by cross-validation as will be described below, a discriminant model expression is generated, and the success or failure of target decoding is determined. First, the discriminant model expression is created from the brain wave data at the time of presentation of target and non-target test stimuli in remaining games (the second to the eighth games) other than a specific game (for example, the first game) for the decoding success/failure determination, and then a discrimination score is calculated for each of the stimulus events in the specific game (the first game) to perform the decoding success/failure determination. For the decoding success/failure determination for another game (for example, the second game), a discriminant model expression generated from the data of all of the remaining games (the first and the third to the eighth games) except for the other game is used. By thus eliminating the data as the object of discrimination from the model expression generation process, overestimation during the decoding success/failure determination can be avoided.

(b-2) how to Determine Discrimination Score

For example, a discrimination score (y) corresponding to one presentation of each image (visual stimulus) is calculated according to a linear discriminant function expressed by the following expression.

$$y = \sum_{i}^{n} w_i x_i + c \qquad \text{[Expression 1]}$$

In the expression of y, x is the value of brain wave data (voltage) at a certain point in time of a certain channel. As to the type of x, there are as many types (n) as the product of the number of channels (which corresponds to the number of measurement locations because the brain wave data are obtained at a plurality of measurement locations on the scalp of the head of the test subject) and data points. A weighting coefficient w and a constant term c for the respective brain wave data may be determined by linear discriminant analysis.

An accumulated discrimination score may be determined by adding up the discrimination scores for the number of times of stimulus presentations for each test stimulus event. Alternatively, an arithmetic mean may be calculated.

(b-3) Cognitive Function Evaluation Process

Figure 3:
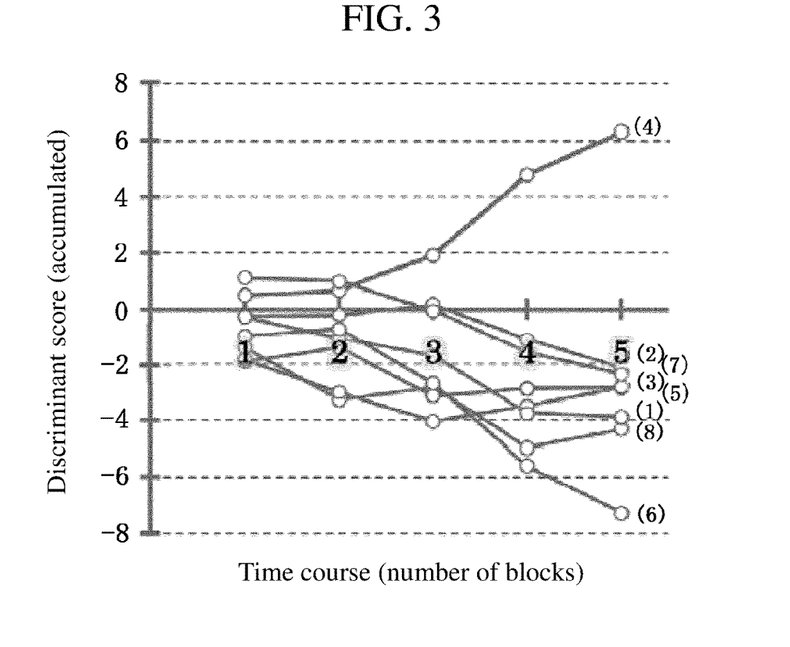
FIG. 3 is a diagram illustrating a discrimination score according to the first embodiment.

FIG. 3 shows a graph illustrating the transition of discrimination scores in the case of a non-handicapped person according to the present embodiment. In FIG. 3, the vertical axis shows the accumulated discrimination score, and the horizontal axis shows time course by way of the number of blocks (first to fifth blocks). It will be seen that, as the discrimination scores of brain wave data for each test stimulus in each block during the execution of the cognitive task of counting the target are accumulated, the accumulated discrimination score for the specific test stimulus event (4) exceeds 6 and shows the highest value after accumulation for five blocks. The accumulated discrimination scores for the other test stimulus events (1), (2), (3), and (5) to (8) becomes lower and stabilized as the blocks are accumulated.

Figure 4:
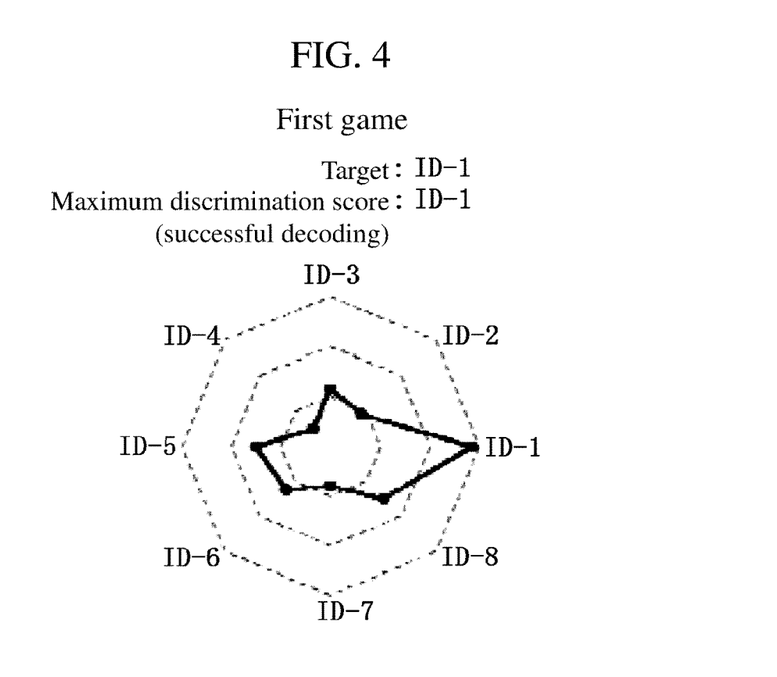
FIG. 4 is a diagram illustrating the first embodiment.

FIG. 4 shows a radar chart illustrating the discrimination scores for eight test stimulus events in the first game in which the target taught was ID-1 (such as star shape). In FIG. 4, the discrimination score for ID-1 is greater than the other discrimination scores and maximized. Accordingly, this is an example of successful decoding where the target taught matches the event of the maximum discrimination score.

Figure 5:
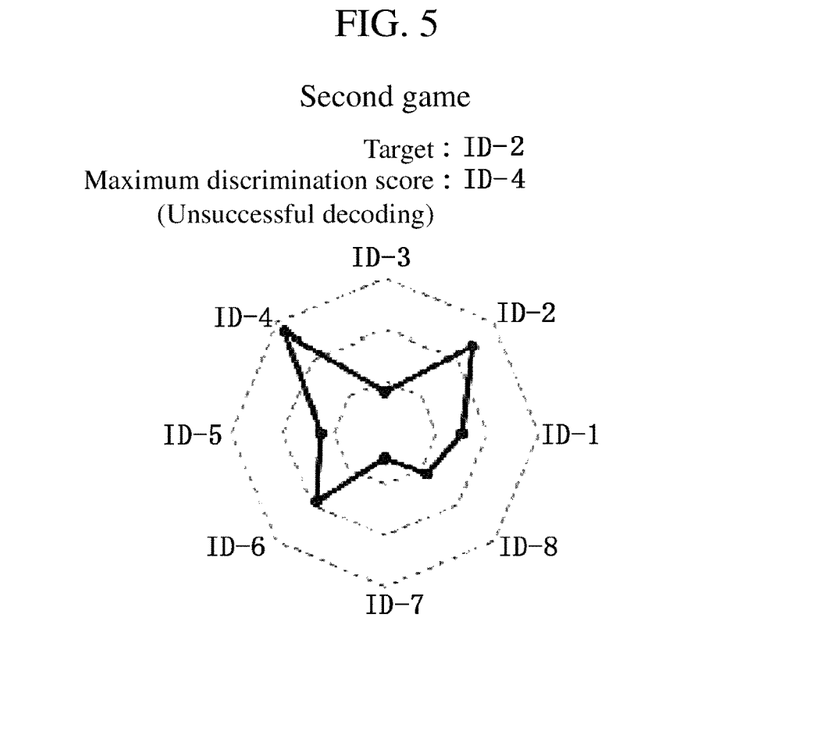
FIG. 5 is a diagram illustrating the first embodiment.

FIG. 5 shows a radar chart illustrating the discrimination scores of eight test stimulus events in the second game in which the target taught was ID-2 (for example, triangle). In FIG. 5, because the discrimination score for ID-4 is greater than the other discrimination scores and maximized, this is an example of unsuccessful decoding where the target taught does not match the event of the maximum discrimination score.

The number of the cases of successful decoding where the target taught matches the event of the maximum discrimination score is divided by the number of the entire cases (the sum of the number of cases of unsuccessful decoding, where the target taught does not match the target of the maximum discrimination score, and the number of cases of successful decoding) to obtain a numerical value which is considered the decoding accuracy. When the implementation involves eight test stimulus events and all of the eight are taught as targets, the decoding accuracy will be 0/8 to 8/8.

Figure 6:
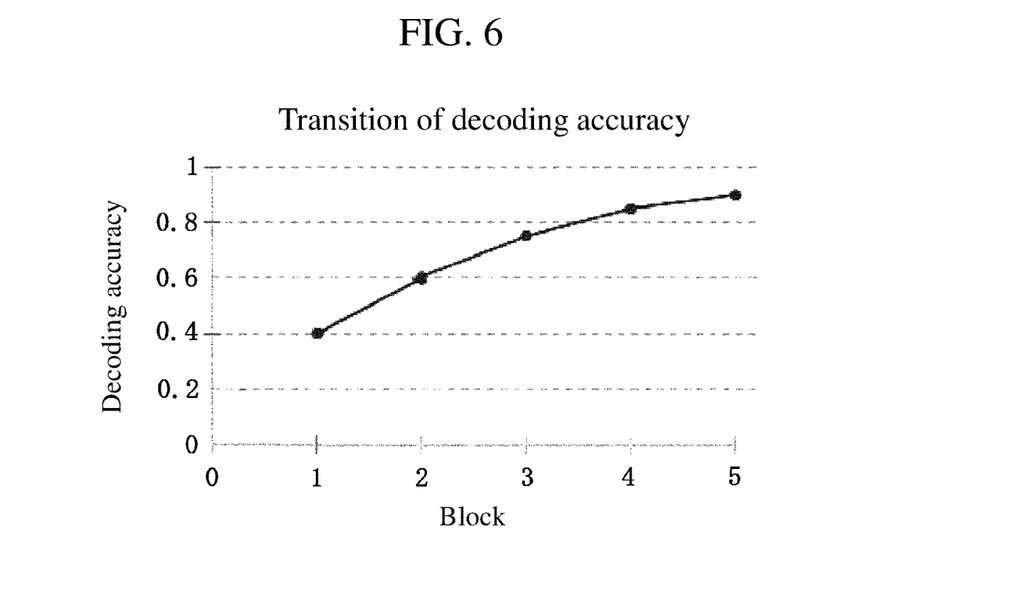
FIG. 6 is a diagram illustrating decoding accuracy in the first embodiment.

FIG. 6 shows a graph illustrating the transition of decoding accuracy according to the present embodiment. In FIG. 6, the vertical axis shows decoding accuracy, and the horizontal axis shows the time course in terms of the number of blocks (from first to fifth blocks). While FIG. 6 illustrates an example of implementation using the accumulated discrimination score, decoding accuracy may be determined from the discrimination score of brain wave data for each block during the execution of the cognitive task of counting the target. For example, an average value of the discrimination scores for brain wave data for the respective blocks may be used.

It is seen from FIG. 6 that the decoding accuracy generally increases as the number of blocks increases, and that, according to the present embodiment, the decoding accuracy exceeds 0.8 in the final fifth block. However, even if the final decoding accuracy is the same, there may be cases where the decoding accuracy remains high from the initial block and follows a gradual course, or cases where the decoding accuracy starts low in the initial block and then rapidly increases. Accordingly, when individual differences or experiment condition differences are analyzed, the cognitive function evaluation may be performed with increased accuracy by referring to the transition of decoding accuracy.

From the results of previous preliminary experiments, it has been observed that when there is cognitive function impairment, the decoding accuracy value tends to be lower than when there is no such impairment. Accordingly, by comparing the decoding accuracy data from a group of persons with no cognitive function impairment with the decoding accuracy of the test subject, the presence or absence of cognitive function impairment and the degree of impairment can be evaluated. Because a single numerical index of decoding accuracy is used, the evaluation can be performed objectively and instantaneously by appropriately setting a threshold value on the basis of the numerical value from the group of non-handicapped persons. In addition, by comparison with the past decoding accuracy for the same test subject, a change in cognitive function impairment can be clarified.

Also, the decoding accuracy for the non-handicapped person tends to increase as the time course (the number of blocks) progresses. When the cognitive function has impairment, the increasing tendency of decoding accuracy may not be observed, depending on the degree or cause of the impairment. Accordingly, by comparing the time course tendency of the test subject's decoding accuracy with that of a group of non-handicapped persons, the presence or absence of cognitive function impairment and the degree of impairment can be evaluated.

In FIG. 6, when attention is only focused on the decoding accuracy in the final block, the accuracy only takes limited values (any of nine values in the case of eight games) in accordance with the number of times of successful decoding, from the case where decoding is entirely unsuccessful (0/8) to the case where decoding is entirely successful (8/8). On the other hand, by focusing on the integrated value of the curves of decoding accuracy, for example, as a technique for expressing the accuracy in numerical value including the transition of decoding accuracy through to the final block, it becomes possible to evaluate cognitive function using more various values.

While the embodiment has been described with reference mainly to a visual stimulus as the test stimulus, a stimulus other than a visual stimulus, such as a hearing stimulus, a contact stimulus, or an odor stimulus may be given to measure and analyze the corresponding brain wave. The evaluation result may be displayed on a display means such as a display apparatus, or may be audibly announced.

Second Embodiment

Figure 7:
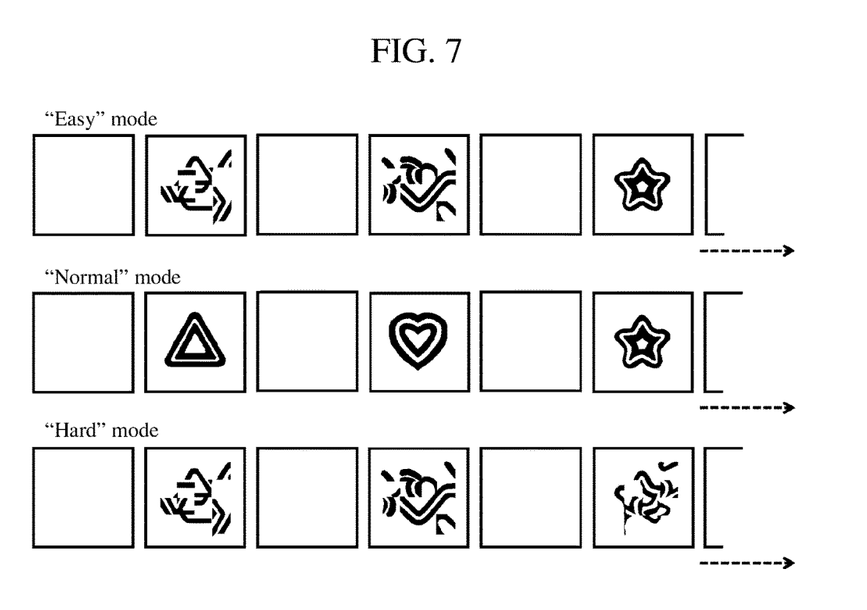
FIG. 7 is a diagram illustrating stimulus event groups with different difficulty levels in the second embodiment.

The second embodiment will be described with reference to the drawings. FIG. 7 is a diagram schematically illustrating stimulus events according to the present embodiment. The present embodiment is characterized in that the stimulus events used during the execution of a cognitive task have different difficulty levels. The apparatus used may be similar to the apparatus according to the first embodiment. As illustrated in FIG. 7, there are prepared a "normal mode" with normal cognitive difficulty level; an "easy mode" with low difficulty level; and a "hard mode" with high difficulty level. The test stimulus events used in the normal mode may be the same as the stimuli described with reference to the first embodiment.

According to the present embodiment, brain wave analysis is performed using at least two stimulus event groups having different levels of difficulty distinguishing between the stimulus events, such as the above three modes, as the stimulus events. With respect to a first group of a plurality of stimulus events, brain waves caused by the plurality of stimulus events comprising a target and non-targets are analyzed and processed to determine a first decoding accuracy. Then, with respect to a second group of a plurality of stimulus events having different levels of difficulty distinguishing between the events from the first plurality of stimulus events, a second decoding accuracy is determined. Based on the first and second decoding accuracy values and the difficulty levels, a process for evaluating cognitive function is performed to obtain a cognitive function evaluation result.

In order to set the visual stimulus difficulty levels, conventional stimulus events for evaluating the cognitive function difficulty level may be used. Further, when an image of, e.g., a figure, an illustration, a drawing, or a photograph is used, the image may be divided into a plurality of parts and then shuffled so as to manipulate the ambiguity of the image, such as a figure. For example, in the easy mode in FIG. 7, with respect to the stimulus events other than the target (star), the figures used are obtained by dividing the normal mode figures into 16 parts and then shuffling by 50%. In the hard mode in FIG. 7, with respect to the stimulus events including the target, the figures used are obtained by dividing the normal mode figures into 16 parts and then shuffling by 50%. The cognitive difficulty level of a figure may be manipulated by, besides shuffling, various known image processing for image obfuscation, such as obscuring a part of the image, pixilation, adding noise, or clouding, whereby the image can be easily processed.

FIG. 8 shows a diagram illustrating changes in the event-related potential of a test subject when test stimuli of normal mode, easy mode, and hard mode were used. Averaged brain waveforms for all channels are shown, where the normal mode is indicated by solid line, the easy mode is indicated by dotted line, and the hard mode is indicated by broken line. The waveforms are examples of the brain waves of a non-handicapped person in response to the target. It is seen that as the difficulty level increases, the latency of event-related potential is extended and the amplitude is decreased.

According to the present embodiment, as illustrated in FIG. 7, three difficulty levels are set by manipulating the ambiguity of the figures, and the cognitive function level in the brain is estimated by brain wave decoding. The brain wave decoding accuracy may be determined by the same method as in the first embodiment.

Figure 9:
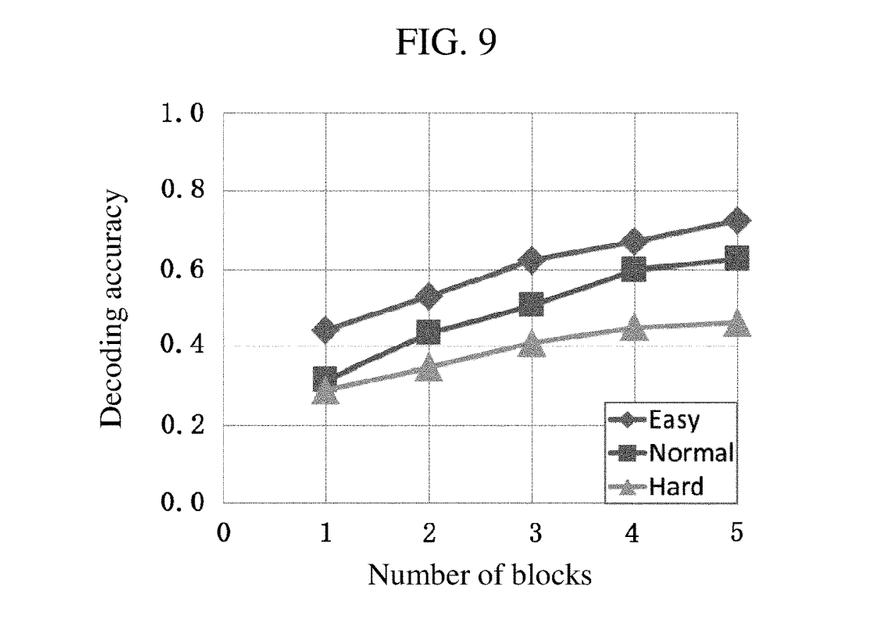
FIG. 9 is a diagram illustrating the relationship between decoding accuracy and time course (the number of blocks) in the stimulus event groups with different difficulty levels in the second embodiment.

When an experiment was conducted on 10 non-handicapped persons, it was confirmed that the accuracy of target prediction by brain wave decoding decreases as the difficulty level of individual cognitive tasks is raised. FIG. 9 illustrates changes in decoding accuracy over a time course (the number of blocks) in the case of test stimuli of normal mode, easy mode, and hard mode. It is seen that the decoding accuracy increases in any of the modes as the number of blocks increases. Compared to normal mode, the easy mode has high decoding accuracy, while the hard mode has lower decoding accuracy. This indicates that the setting of the cognitive task difficulty levels is appropriate. The difficulty level setting for the stimulus events may be prepared in accordance with the value of decoding accuracy in a group of non-handicapped persons or a change in the value.

Figure 10:
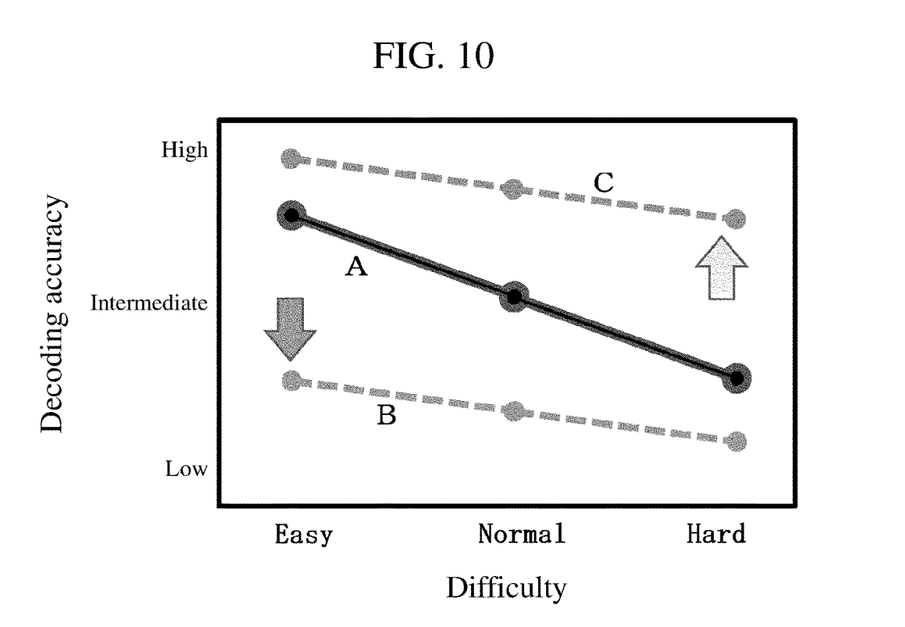
FIG. 10 is a diagram illustrating the relationship between decoding accuracy and difficulty level in the stimulus event groups with different difficulty levels in the second embodiment.

An analysis method will be described for the implementation of stimulus presentation in modes with different difficulty levels and brain wave measurement with respect to a test subject whose cognitive function may possibly be higher or lower than normal. FIG. 10 illustrates the relationship between difficulty level and decoding accuracy. The vertical axis shows decoding accuracy, while the horizontal axis shows difficulty level which varies, from left to right, from low to normal to high. Line A corresponds to a non-handicapped person; line B to a test subject with low cognitive function; and line C to a test subject with high cognitive function or to the case in which an increase in cognitive function was observed after repeated training with the cognitive task according to the present embodiment or other cognitive tasks. It is seen that with respect to the non-handicapped person, the decoding accuracy tends to decrease at a constant rate as the difficulty level increases. On the other hand, in the case of the test subject with low level of cognitive function, the decoding accuracy is low throughout, that the decoding accuracy is low even when the difficulty level is low, and that the decoding accuracy varying tendency is small. This shows that by comparing the correlations between difficulty level and decoding accuracy, the presence or absence of cognitive function impairment and the degree of impairment can be evaluated. For example, by expressing the decoding accuracy change rate in response to a difficulty level change in numerical value, comparison with the numerical value from a group of non-handicapped persons can be easily made. In addition, comparison with the past data of the same test subject can be easily made by utilizing the numerical index. Similar reasoning may be used to evaluate the test subject with possibly higher-than-normal cognitive function.

As illustrated in FIG. 10, the cognitive function of the test subject can be accurately evaluated using the decoding accuracy value or a change in the decoding accuracy value. Accordingly, in addition to the presence or absence of cognitive function impairment and the degree of impairment, a decrease or increase in the cognitive function of the test subject can be detected, providing an index of the effect of cognitive rehabilitation.

In FIG. 9 and FIG. 10, the decoding accuracy is expressed in numerical value in nine steps from 0/8 to 8/8. In another technique, the decoding accuracy may be expressed in numerical value by using an integrated value of a curve indicating the decoding accuracy. The numerical value may comprise the number of blocks when a specific decoding accuracy is reached.

In the preparation stage for setting a stimulus event, the stimulus event may be set by conducting an experiment on a number of non-handicapped persons using brain wave decoding or a bodily input operation, and investigating how the target prediction accuracy by brain wave decoding worsens as the difficulty level of the cognitive task is increased. By appropriately setting the cognitive task difficulty level, it may be suggested that there is a high risk of cognitive function decrease when a test subject below a normal range is detected. For example, mild form of a stroke or the initial state of dementia can be detected early so that various measures can be taken. In addition, even for a non-handicapped person, a "brain training" effect of increasing the decoding accuracy by training with a problem can be expected.

Data regarding the connection between a difficulty level change and decoding accuracy may be accumulated so as to determine the presence or absence of cognitive function impairment or the degree of impairment, or the cause of cognitive function impairment, for example, based on the connection. The connection may include positive and negative correlations between difficulty level change and decoding accuracy, other correlations, and a ratio of difficulty level change to decoding accuracy. The connection between difficulty level change and decoding accuracy may also be included in the cognitive function evaluation index, whereby more accurate cognitive function evaluation can be made.

Third Embodiment

In the first and the second embodiments, the number of blocks has been fixed. The present embodiment is characterized in that the number of blocks is not fixed.

When the discrimination score for each test stimulus in each block is accumulated as in FIG. 3 described with reference to the first embodiment, the accumulated discrimination score tends to be increased as the number of blocks increases. Accordingly, the number of blocks at which the accumulated discrimination score has reached (or exceeded) a specific threshold value may be used as an index for cognitive function evaluation. According to the present embodiment, the maximum number of blocks per game is set to be slightly more than normal (for example, 10 blocks when normally five blocks), and the stimulus presentation is terminated for real-time decoding during the experiment. For example, in FIG. 3, the block number when the accumulated discrimination score becomes 3 or more in a certain game is the fourth block, so that the stimulus presentation is terminated at this point and a value obtained by dividing one by the number of blocks is defined as the decoding speed. The decoding speed becomes maximum (1) when the discrimination score has already reached the threshold value in the initial block, and the decoding speed value becomes smaller as the required blocks increase. If the accumulated discrimination score for any of the stimulus types has not reached the threshold value at the end of the maximum block, or if the accumulated discrimination score for a non-target stimulus type has reached the threshold value before the target, the decoding speed is considered 0 (1/infinity). In this way, the decoding speeds for all games are calculated, and then an arithmetic mean of the speeds is set as an evaluation index for each test subject. By comparing the average decoding speed of each test subject with the average decoding speed of a group of non-handicapped persons, it can be evaluated that the cognitive function is high if the value is greater or low if the value is smaller.

When an experiment is performed in this system, it is necessary to perform a preliminary experiment with fixed blocks and to conduct sufficient data collection for enabling the generation of a discriminant model expression or setting of an appropriate threshold value (such that, for example, the decoding accuracy in all games becomes 0.8). On the other hand, in an experiment in which the present embodiment is implemented, a decoding success/failure determination can be made in real-time according to a discriminant model expression created beforehand without using cross-validation by the above-described off-line analysis. In addition, the main experiment can be conducted after confirming whether high-quality brain wave data have been acquired at the preliminary experiment stage.

As in the second embodiment, by plotting on the vertical axis the number of blocks at which the accumulated discrimination score becomes equal to or greater than a threshold value in modes (difficulty level conditions) with different difficulty levels, the results for the test subject can be compared and evaluated with a group of non-handicapped persons. For example, in the case of a group of non-handicapped persons, the average decoding speed decreases from 0.8 to 0.6 and to 0.4 respectively for the easy mode, normal mode, and hard mode, whereas for a certain test subject, the average decoding speed in the three modes may become 0.3, 0.2, and 0.1, respectively. Thus, in addition to the average decoding speed in each mode, the connection between a difficulty level change and an average decoding speed can be grasped in terms of the slope of the approximation line (curve), enabling more detailed evaluation of the cognitive function transformation.

As described above, according to the present embodiment, stimulus presentation may be terminated when the accumulated discrimination score has reached a threshold value. By performing this termination process, cognitive function evaluation can be performed in a shorter time than when not terminated. In addition, the test subject can also confirm the success or failure of decoding in each game, so that the person can experience the present evaluation system as if having fun with a game.

As in the third embodiment, according to the first and the second embodiments, if a data acquisition experiment for generating a discriminant model is performed in a preliminary experiment before the main experiment, the decoding result can be fed back to the test subject for each game in the main experiment using the discriminant model. In addition, according to any of the first to the third embodiments, if a discriminant model is created in advance, comparative data about the magnitude of the accumulated discrimination score for each stimulus type from the first block to the last block (including a block made final by termination) in each game can be fed back to the test subject. In this way, the present evaluation system can be experienced on an enhanced real-time basis and as if playing a game.

The cognitive function evaluation techniques according to the first to the third embodiments may be used individually or in combination. For example, a discrimination score or decoding accuracy is determined, and then cognitive function can be evaluated on the basis of the value of one or more of the discrimination score, the decoding accuracy, any of time courses (the number of blocks), and decoding speed. The discrimination score or decoding accuracy may be determined for each of different difficulty levels, and then cognitive function may be evaluated on the basis of the connection between one or more of the discrimination score, the decoding accuracy, any of time-courses, and decoding speed with the difficulty levels.

The examples described with reference to the embodiments and the like are intended to aid the reader in understanding the invention, which is not limited to the embodiments.

REFERENCE SIGNS LIST

1 Presentation of stimulus to test subject
3 Electroencephalograph electrodes on test subject
4 Brain wave amplifier
6 Computer

What is claimed:

1. A cognitive function evaluation apparatus, comprising:
a processing unit configured to:
receive brain wave data representative of a brain wave of a user measured by a brain wave amplifier, wherein the brain wave is measured at least partially concurrently with administration of a first test to the user, the processing unit further configured to administer the first test at least in part by presenting a plurality of stimulus events to the user at each of a plurality of times, wherein the plurality of stimulus events comprises a target stimulus event and one or more non-target stimulus events, and wherein administration of the first test comprises presenting the plurality of stimulus events to the user in blocks, each block corresponding to a respective sequence of the plurality of stimulus events;
determine a respective discrimination score for each stimulus event for each block;
determine a respective accumulated discrimination score for each stimulus event across the blocks;
determine a particular stimulus event corresponding to the largest respective accumulated discrimination score;
determine a decoding result associated with the first test based at least in part on whether the particular stimulus event is the target stimulus event, wherein the decoding result is a successful result if the particular stimulus event is the target stimulus event or the decoding result is a failure result if the particular stimulus event is different from the target stimulus event;
determine a decoding accuracy for the user, wherein the decoding accuracy is associated with administration of a plurality of tests to the user including the first test, wherein the decoding accuracy is a ratio of a number of successful decoding results to a total number of decoding results for the plurality of tests administered to the user, and wherein the total number of decoding results comprises the decoding result associated with the first test administered to the user;
determine a threshold decoding accuracy value associated with administration of the plurality of tests to a group of users in which a cognitive function impairment is absent, wherein the threshold decoding accuracy value is a ratio of a number of successful decoding results to a total number of decoding results for the plurality of tests administered to the group of users;
determine that the decoding accuracy for the user is less than the threshold decoding accuracy value; and
determine that the cognitive function impairment is present in the user based at least in part on determining that the decoding accuracy for the user is less than the threshold decoding accuracy value.

2. The cognitive function evaluation apparatus of claim 1, wherein the processing unit is further configured to:
determine that the decoding accuracy for the user is greater than a historical decoding accuracy for the user; and
determine that a degree of the cognitive function impairment present in the user has been reduced between a first time at which the historical decoding accuracy was determined and a second time at which the decoding accuracy is determined.

3. The cognitive function evaluation apparatus of claim 1, wherein the processing unit is further configured to:
determine a first rate of change in the decoding accuracy for the user as the blocks are presented to the user;
determine a second rate of change in a decoding accuracy associated with the group of users in which the cognitive function impairment is absent as the blocks are presented to the group of users; and
determine that the cognitive function impairment is present in the user further based at least in part on a deviation between the first rate of change and the second rate of change.

4. The cognitive function evaluation apparatus of claim 1, wherein presentation of the plurality of stimulus events to the user comprises an instruction for the user to count a number of times the target stimulus event is presented.

5. The cognitive function evaluation apparatus of claim 1, wherein each block comprises a respective different pseudo-random sequence of the plurality of stimulus events.

6. The cognitive function evaluation apparatus of claim 5, wherein the target stimulus event is different for two or more respective pseudo-random sequences.

7. A cognitive function evaluation method, comprising:
administering a first test to a user, wherein administering the first test comprises presenting a plurality of stimulus events to the user at each of a plurality of times, the plurality of stimulus events comprising a target stimulus event and one or more non-target stimulus events, and wherein presenting the plurality of stimulus events comprises presenting the plurality of stimulus events to the user in blocks, each block corresponding to a respective sequence of the plurality of stimulus events;
measuring, using a brain wave amplifier, a brain wave of the user at least partially concurrently with the administering of the first test to the user; and
using a processing unit:
generating brain wave data representative of the measured brain wave; and
analyzing the brain wave data to determine that cognitive function impairment is present in the user, wherein analyzing the brain wave data comprises:
determining a respective discrimination score for each stimulus event for each block;
determining a respective accumulated discrimination score for each stimulus event across the blocks;
determining a particular stimulus event corresponding to the largest respective accumulated discrimination score;
determining a decoding result associated with the first test based at least in part on whether the particular stimulus event is the target stimulus event, wherein the decoding result is a successful result if the particular stimulus event is the target stimulus event or the decoding result is a failure result if the particular stimulus event is different from the target stimulus event;
determining a decoding accuracy for the user, wherein the decoding accuracy is associated with administration of a plurality of tests to the user including the first test, wherein the decoding accuracy is a ratio of a number of successful decoding results to a total number of decoding results for the plurality of tests administered to the user, and wherein the total number of decoding results comprises the decoding result associated with the first test administered to the user;
determining a threshold decoding accuracy value associated with administration of the plurality of tests to a group of users in which cognitive function impairment is absent, wherein the threshold decoding accuracy value is a ratio of a number of successful decoding results to a total number of decoding results for the plurality of tests administered to the group of users;
determining that the decoding accuracy for the user is less than the threshold decoding accuracy value; and
determining that the cognitive function impairment is present in the user based at least in part on determining that the decoding accuracy for the user is less than the threshold decoding accuracy value.

8. The cognitive function evaluation method of claim 7, further comprising:
determining that the decoding accuracy for the user is greater than a historical decoding accuracy for the user; and
determining that a degree of the cognitive function impairment present in the user has been reduced between a first time at which the historical decoding accuracy was determined and a second time at which the decoding accuracy is determined.

9. The cognitive function evaluation method of claim 7, further comprising:
determining a first rate of change in the decoding accuracy for the user as the blocks are presented to the user;
determining a second rate of change in a decoding accuracy associated with the group of users in which the cognitive function impairment is absent as the blocks are presented to the group of users; and
determining that the cognitive function impairment is present in the user further based at least in part on a deviation between the first rate of change and the second rate of change.

10. The cognitive function evaluation method of claim 7, wherein presenting the plurality of stimulus events to the user comprises presenting an instruction for the user to count a number of times the target stimulus event is presented.

11. The cognitive function evaluation method of claim 7, wherein each block comprises a respective different pseudo-random sequence of the plurality of stimulus events.

12. The cognitive function evaluation method of claim 11, wherein the target stimulus event is different for two or more respective pseudo-random sequences.

13. A cognitive function evaluation system, comprising:
a stimulus presentation apparatus that administers a first test to a user, wherein administering the first test comprises presenting a plurality of stimulus events to the user at each of a plurality of times, the plurality of stimulus events comprising a target stimulus event and one or more non-target stimulus events, and wherein presenting the plurality of stimulus events comprises presenting the plurality of stimulus events to the user in blocks, each block corresponding to a respective sequence of the plurality of stimulus events;
a brain wave amplifier that measures a brain wave of the user at least partially concurrently with administering the first test to the user and generates brain wave data representative of the measured brain wave; and
a processing apparatus that analyzes the brain wave data to determine that cognitive function impairment is present in the user, wherein analyzing the brain wave data comprises:
determining a respective discrimination score for each stimulus event for each block;
determining a respective accumulated discrimination score for each stimulus event across the blocks;
determining a particular stimulus event corresponding to the largest respective accumulated discrimination score;
determining a decoding result associated with the first test based at least in part on whether the particular stimulus event is the target stimulus event, wherein the decoding result is a successful result if the particular stimulus event is the target stimulus event or the decoding result is a failure result if the particular stimulus event is different from the target stimulus event;

determining a decoding accuracy for the user, wherein the decoding accuracy is associated with administration of a plurality of tests to the user including the first test, wherein the decoding accuracy is a ratio of a number of successful decoding results to a total number of decoding results for the plurality of tests administered to the user, and wherein the total number of decoding results comprises the decoding result associated with the first test administered to the user;

determining a threshold decoding accuracy value associated with administration of the plurality of tests to a group of users in which cognitive function impairment is absent, wherein the threshold decoding accuracy value is a ratio of a number of successful decoding results to a total number of decoding results for the plurality of tests administered to the group of users;

determining that the decoding accuracy for the user is less than the threshold decoding accuracy value; and determining that the cognitive function impairment is present in the user based at least in part on determining that the decoding accuracy for the user is less than the threshold decoding accuracy value.

14. The cognitive function evaluation system of claim 13, wherein the processing apparatus:
determines that the decoding accuracy for the user is greater than a historical decoding accuracy for the user; and
determines that a degree of the cognitive function impairment present in the user has been reduced between a first time at which the historical decoding accuracy was determined and a second time at which the decoding accuracy is determined.

15. The cognitive function evaluation system of claim 13, wherein the processing apparatus:
determines a first rate of change in the decoding accuracy for the user as the blocks are presented to the user;
determines a second rate of change in a decoding accuracy associated with the group of users in which the cognitive function impairment is absent as the blocks are presented to the group of users; and
determines that the cognitive function impairment is present in the user further based at least in part on a deviation between the first rate of change and the second rate of change.

16. The cognitive function evaluation system of claim 13, wherein presenting the plurality of stimulus events to the user comprises presenting an instruction for the user to count a number of times the target stimulus event is presented.

17. The cognitive function evaluation system of claim 13, wherein each block comprises a respective different pseudo-random sequence of the plurality of stimulus events.

18. The cognitive function evaluation system of claim 17, wherein the target stimulus event is different for two or more respective pseudo-random sequences.

* * * * *